United States Patent
Han et al.

(10) Patent No.: US 11,113,611 B2
(45) Date of Patent: Sep. 7, 2021

(54) METHOD AND ELECTRONIC APPARATUS FOR PREDICTING ELECTRONIC STRUCTURE OF MATERIAL

(71) Applicant: KOREA INSTITUTE OF SCIENCE AND TECHNOLOGY, Seoul (KR)

(72) Inventors: Sang Soo Han, Seoul (KR); Byung Chul Yeo, Seoul (KR); Chansoo Kim, Seoul (KR); Donghun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 871 days.

(21) Appl. No.: 15/892,774

(22) Filed: Feb. 9, 2018

(65) Prior Publication Data
US 2019/0065968 A1    Feb. 28, 2019

(30) Foreign Application Priority Data
Aug. 28, 2017    (KR) .......................... 10-2017-0108850

(51) Int. Cl.
| | | |
|---|---|---|
| *G06N 5/04* | (2006.01) | |
| *G06F 17/16* | (2006.01) | |
| *G06N 20/00* | (2019.01) | |
| *G06F 16/901* | (2019.01) | |
| *G16C 60/00* | (2019.01) | |

(Continued)

(52) U.S. Cl.
CPC ........... *G06N 5/04* (2013.01); *G06F 16/9024* (2019.01); *G06F 17/16* (2013.01); *G06N 20/00* (2019.01); *G16C 10/00* (2019.02); *G16C 20/70* (2019.02); *G16C 60/00* (2019.02)

(58) Field of Classification Search
CPC .......... G06N 5/04; G06N 20/00; G16C 20/70; G16C 60/00; G16C 10/00; G06F 16/9024; G06F 17/16
See application file for complete search history.

(56) References Cited

U.S. PATENT DOCUMENTS

| | | | |
|---|---|---|---|
| 8,044,544 B2 | 10/2011 | Sone et al. | |
| 2010/0185716 A1* | 7/2010 | Nakamura | ............... G06F 17/16 708/650 |
| 2017/0124482 A1* | 5/2017 | Yoo | ........................ G06N 20/00 |

FOREIGN PATENT DOCUMENTS

| | | | | |
|---|---|---|---|---|
| CA | 2012142 A1 * | 9/1991 | ............. | G01N 37/00 |
| JP | 2007-120640 A | 5/2007 | | |

(Continued)

OTHER PUBLICATIONS

Korean Office Action dated Jul. 16, 2018.

*Primary Examiner* — Tarun Sinha
*Assistant Examiner* — Lal C Mang
(74) *Attorney, Agent, or Firm* — Rabin & Berdo, P.C.

(57) ABSTRACT

A method of predicting an electronic structure of a material by an electronic apparatus includes receiving user's input data about elements constituting the material; applying the received user's input data to a trained model for estimating a state density of the material; and outputting a first graph representing energy level-by-level state densities of the material output from the trained model, wherein the trained model is trained to generate the first graph based on a plurality of second graphs representing pre-calculated energy level-by-level state densities respectively corresponding to a plurality of pre-input data about elements of various materials and the plurality of pre-input data.

11 Claims, 8 Drawing Sheets

(51) Int. Cl.
*G16C 10/00* (2019.01)
*G16C 20/70* (2019.01)

(56) References Cited

FOREIGN PATENT DOCUMENTS

| | | | | |
|---|---|---|---|---|
| KR | 10-2010-0042453 A | | 4/2010 | |
| WO | H0862162 A | * | 3/1996 | ............ G16C 10/00 |
| WO | WO-2011036952 A1 | * | 3/2011 | ............ G06F 17/16 |

* cited by examiner

METHOD AND ELECTRONIC APPARATUS FOR PREDICTING ELECTRONIC STRUCTURE OF MATERIAL

CROSS-REFERENCE TO RELATED APPLICATION

This application claims the benefit of Korean Patent Application No. 10-2017-0108850, filed on Aug. 28, 2017, in the Korean Intellectual Property Office, the disclosure of which is incorporated herein in its entirety by reference.

BACKGROUND

1. Field

One or more embodiments relate to methods and electronic apparatuses for predicting electronic structures of materials.

2. Description of the Related Art

The physical properties of a material, such as metallicity and electrical conductivity, may be determined from the electronic structure of the material (e.g., the structure of an energy band of electrons).

New materials have been developed through a method of finding the physical properties of a material from the electronic structure of the material. For example, a semiconductor material has been developed by using information about a band gap, that is, the energy necessary to excite electrons from a valence band to a conduction band level. Also, a chemical material such as a catalyst or a secondary battery has been developed based on the electronic structure of a material.

Density of State (DOS) information is mainly used to find the electronic structure of a material. In detail, energy-dependent state densities may be graphed to find the electronic structure and physical properties of a material.

In the related art, the state density of a material is estimated by methods such as an empirical method, a tight binding method, a density functional theory (DFT) method, and a Beyond DFT method, and then, the electronic structure of the material is predicted by using the estimated state density. However, a conventional method for predicting the electronic structure has a problem in that the faster the time for using the method, the lower the accuracy of the method, or the longer the time for using the method, the higher the accuracy of the method. For example, when the DFT method, which is the most commonly used method to computationally estimate the state density of a material, is used, it takes about 2 to 3 days to estimate the state density of a single material. Thus, use of the DFT method is time-consuming and expensive.

Therefore, since the state densities of a plurality of materials are required to develop a new material, there is a need for a method of estimating the state density of a material fast and with high accuracy.

SUMMARY

One or more embodiments include methods and electronic apparatuses for predicting electronic structures of materials.

Additional aspects will be set forth in part in the description which follows and, in part, will be apparent from the description, or may be learned by practice of the presented embodiments.

According to one or more embodiments, a method of predicting an electronic structure of a material by an electronic apparatus includes: receiving user's input data about elements constituting the material; applying the received user's input data to a trained model for estimating a state density of the material; and outputting a first graph representing energy level-by-level state densities of the material output from the trained model, wherein the trained model is trained to generate the first graph based on a plurality of second graphs representing pre-calculated energy level-by-level state densities corresponding respectively to a plurality of pre-input data about elements constituting materials and the plurality of pre-input data.

The trained model may be trained to convert the plurality of second graphs into a plurality of lattice images, respectively; determine at least one principal component representing a characteristic of the first graph based on the plurality of lattice images; and generate the first graph based on the at least one principal component.

The trained model may be trained to convert the plurality of lattice images into a plurality of matrixes, respectively; calculate a covariance of the plurality of matrixes; calculate at least one eigenvector and at least one eigenvalue based on the calculated covariance; and determine the at least one principal component based on the at least one eigenvector and the at least one eigenvalue.

The trained model may be trained to determine the number of principal components used to generate the first graph based on the user's input data.

The trained model may be trained to determine at least one principal component used to generate the first graph based on the determined number of principal components.

The trained model may be trained to acquire, from the received user's input data, a d-orbital electron number occupation rate of each of a plurality of elements constituting the material and determine a coefficient of the principal component based on the acquired d-orbital electron number occupation rate.

The d-orbital electron number occupation rate may be determined based on the number of atoms and the d-orbital electron number of each of the elements constituting the material.

According to one or more embodiments, an electronic apparatus for predicting an electronic structure of a material includes: a user input interface configured to receive user's input data about elements constituting the material; a processor configured to apply the received user's input data to a trained model for estimating a state density of the material; and an output interface configured to output a first graph representing energy level-by-level state densities of the material output from the trained model, wherein the trained model is trained to generate the first graph based on a plurality of second graphs representing pre-calculated energy level-by-level state densities corresponding respectively to a plurality of pre-input data about elements constituting materials and the plurality of pre-input data.

The trained model may be trained to convert the plurality of second graphs into a plurality of lattice images, respectively; determine at least one principal component representing a characteristic of the first graph based on the plurality of lattice images; and generate the first graph based on the at least one principal component.

The trained model may be trained to convert the plurality of lattice images into a plurality of matrixes, respectively; calculate a covariance of the plurality of matrixes; calculate at least one eigenvector and at least one eigenvalue based on the calculated covariance; and determine the at least one principal component based on the at least one eigenvector and the at least one eigenvalue.

The trained model may be trained to determine a number of principal components used to generate the first graph based on the user's input data.

The trained model may be trained to determine at least one principal component used to generate the first graph based on the determined number of principal components.

The trained model may be trained to acquire, from the received user's input data, a d-orbital electron number occupation rate of each of a plurality of elements constituting the material and determine a coefficient of the principal component based on the acquired d-orbital electron number occupation rate.

The d-orbital electron number occupation rate may be determined based on the number of atoms and the d-orbital electron number of each of the constituent elements of the material.

According to one or more embodiments, a non-transitory computer-readable recording medium stores a program that, when executed by a computer, performs the above method.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
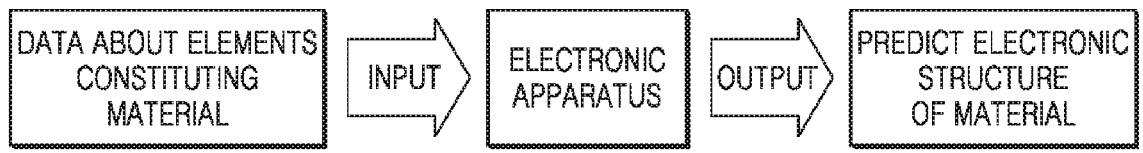
FIG. 1 is a diagram illustrating an example of a method of predicting an electronic structure of a material, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the inventive concept will be described in detail with reference to the accompanying drawings so that those of ordinary skill in the art may easily implement the embodiments. In this regard, the inventive concept may have different forms and should not be construed as being limited to the descriptions set forth herein. In addition, portions irrelevant to the description of the inventive concept will be omitted in the drawings for a clear description of the inventive concept, and like reference numerals will denote like elements throughout the specification.

Some embodiments of the inventive concept may be represented in terms of functional block components and various processing operations. Some or all of these functional blocks may be implemented by any number of hardware and/or software components that execute particular functions. For example, the functional blocks of the inventive concept may be implemented by one or more microprocessors or may be implemented by circuit components for a certain function. Also, for example, the functional blocks of the inventive concept may be implemented in various programming or scripting languages. The functional blocks may be implemented by an algorithm that is executed in one or more processors. Also, the inventive concept may employ the related art for electronic environment setting, signal processing, and/or data processing. Terms such as "mechanism", "element", "unit", and "configuration" may be used in a broad sense, and are not limited to mechanical and physical configurations.

Throughout the specification, when an element is referred to as being "connected" to another element, it may be "directly connected" to the other element or may be "electrically connected" to the other element with one or more intervening elements therebetween. Also, when something is referred to as "including" a component, another component may be further included unless specified otherwise.

Also, connection members or connection lines between elements illustrated in the drawings merely represent examples of physical or logical connections and/or functional connections. In actual devices, the connection between elements may be represented by various alternative or additional functional connections, physical connections, or logical connections.

Also, although terms including ordinals such as "first" or "second" may be used herein to describe various elements or components, these elements or components should not be limited by these terms. These terms are only used to distinguish one element or component from another element or component.

Hereinafter, the inventive concept will be described in detail with reference to the accompanying drawings.

FIG. 1 is a diagram illustrating an example of a method of predicting an electronic structure of a material, according to an embodiment.

Referring to FIG. 1, an electronic apparatus 1000 may receive an input of data about elements constituting a material. The electronic apparatus 1000 may predict an electronic structure of the material based on the data input from a user. The electronic apparatus 1000 may output a prediction result regarding the electronic structure of the material.

According to an embodiment, the data about the elements constituting the material, which is input to the electronic apparatus 1000, may include, but is not limited to, data about the type of the elements constituting the material, the number of atoms thereof, the number of electrons thereof, a chemical formula thereof, and an empirical formula thereof.

According to an embodiment, the electronic apparatus 1000 may predict the electronic structure of the material by applying the data about the number of elements constituting the material, the type of the elements, the number of atoms thereof, the number of electrons thereof, the chemical formula thereof, and the empirical formula thereof, which is input from the user, to a trained model for estimating a state density of the material.

According to an embodiment, the trained model may be trained to generate a graph corresponding to the material input from the user, based on graphs for predicting the electronic structure of the material respectively corresponding to a plurality of pre-input data about elements of various materials. For example, the trained model may be trained to generate an energy level-by-level state density graph of the material input from the user, based on pre-calculated energy level-by-level state density graphs respectively corresponding to a plurality of pre-input data about elements of various materials.

According to an embodiment, the electronic apparatus 1000 may generate a graph for predicting the electronic structure of the material, based on the data about the number of elements constituting the material, the type of the elements, the number of atoms thereof, the number of electrons thereof, the chemical formula thereof, and the empirical formula thereof, the data being input by the user. For example, in order to predict the electronic structure of the material, the electronic apparatus 1000 may generate an energy level-by-level state density graph of the material and output the generated energy level-by-level state density graph.

Figure 2:
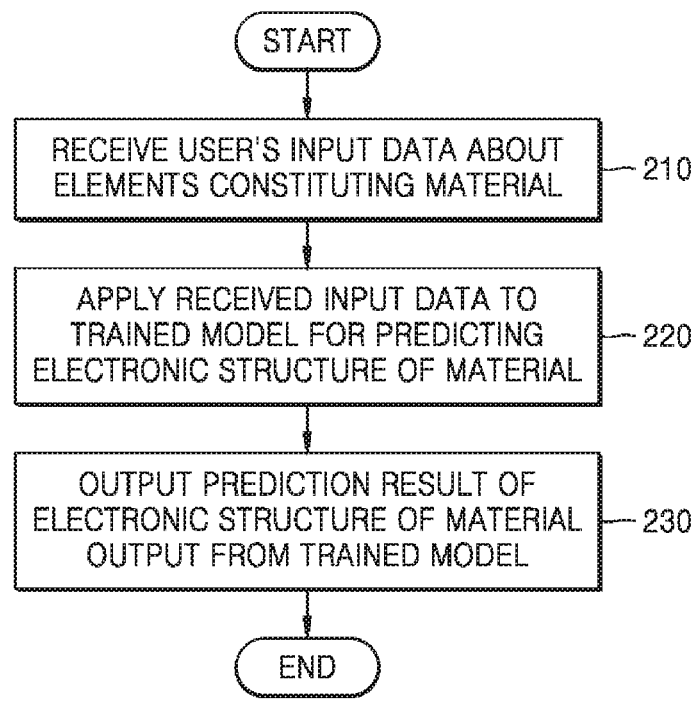
FIG. 2 is a flow diagram of a method of predicting an electronic structure of a material, according to an embodiment.

FIG. 2 is a flow diagram of a method of predicting an electronic structure of a material, according to an embodiment, the method being used by the electronic apparatus 1000.

In operation 210, the electronic apparatus 1000 may receive from a user data about elements constituting a material.

According to an embodiment, the electronic apparatus 1000 may receive from the user data about a number of elements constituting the material, a type of the elements, the number of atoms thereof, the number of electrons thereof, a chemical formula thereof, and an empirical formula thereof, but is not limited thereto.

In operation 220, the electronic apparatus 1000 may apply the data about the elements constituting the material received from the user to a trained model for predicting an electronic structure of the material.

According to an embodiment, the electronic apparatus 1000 may apply the data about the elements constituting the material received from the user to a trained model for estimating a state density of the material. The trained model for estimating the state density of the material will be described below with reference to FIG. 3.

In operation 230, the electronic apparatus 1000 may output an electronic structure prediction result regarding the material output from the trained model.

According to an embodiment, the electronic apparatus 1000 may output atomic structure information such as a lattice constant of the material and state density data of the material from the trained model, but is not limited thereto.

According to an embodiment, the electronic apparatus 1000 may output the state density data of the material as an energy level-by-level state density graph of the material, but is not limited thereto.

According to an embodiment, the energy level-by-level state density graph of the material output from the trained model may be generated based on a principal component determined in the trained model, but is not limited thereto.

According to an embodiment, the energy level-by-level state density graph of the material output from the trained model may be generated based on user's input data about the elements constituting the material, but is not limited thereto.

According to an embodiment, the energy level-by-level state density graph of the material output from the trained model may be generated as a linear combination of a plurality of principal components and a coefficient of each of the plurality of principal components, but is not limited thereto. For example, the energy level-by-level state density graph of the material output from the trained model may be generated using Equation 1.

$$DOS(E) = \alpha_1 \times PC1(E) + \alpha_2 \times PC2(E) + \alpha_3 \times PC3(E) + \alpha_4 \times PC4(E)$$ Equation 1

Herein, $DOS(E)$ is an energy level-by-level state density graph of a material, $PC1(E)$ is an energy level-by-level first principal component graph, $PC2(E)$ is an energy level-by-level second principal component graph, $PC3(E)$ is an energy level-by-level third principal component graph, $PC4(E)$ is an energy level-by-level fourth principal component graph, $\alpha_1$ is a coefficient of a first principal component, $\alpha_2$ is a coefficient of a second principal component, $\alpha_3$ is a coefficient of a third principal component, and $\alpha_4$ is a coefficient of a fourth principal component.

The output of the energy level-by-level state density graph of the material by the electronic apparatus 1000 will be described below with reference to FIGS. 8 and 9.

Figure 3:
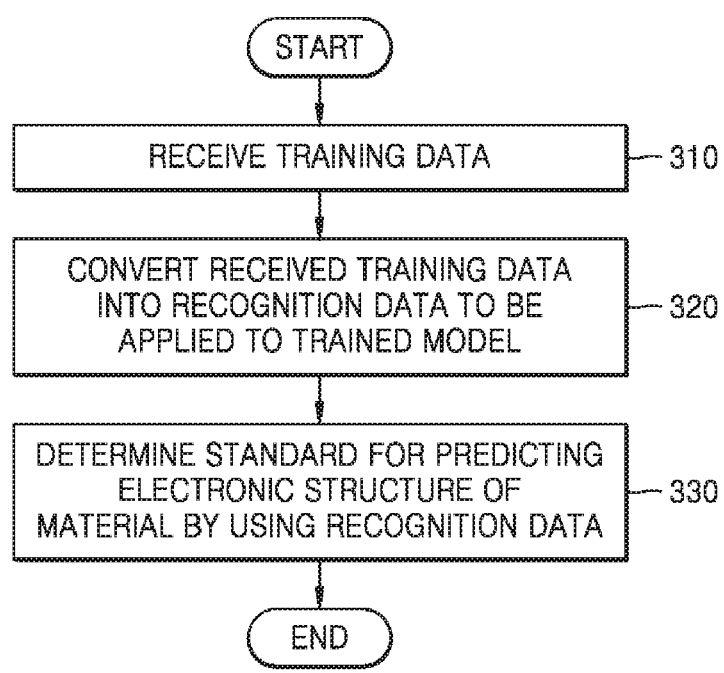
FIG. 3 is a flow diagram of a method of training data for predicting an electronic structure of a material, according to an embodiment.

FIG. 3 is a flow diagram of a method of training data for predicting an electronic structure of a material, according to an embodiment.

In operation 310, the electronic apparatus 1000 may receive from the user training data for training a standard for predicting an electronic structure of a material by using a trained model.

According to an embodiment, the electronic apparatus 1000 may receive data about a plurality of materials and the result of predicting an electronic structure of the plurality of materials as the training data from the user. A plurality of data about the plurality of materials may include, but are not limited to, a number of elements constituting each of the plurality of materials, a type of the elements, the number of atoms thereof, the number of electrons thereof, a chemical formula thereof, and an empirical formula thereof. The result of predicting the electronic structure of the material may include state density data of the material. Also, the state density data of the material may include, but is not limited to, an energy level-by-level state density graph.

In operation 320, the electronic apparatus 1000 may convert the training data received from the user into recognition data to be applied to the trained model. The electronic apparatus 1000 may apply the recognition data to the trained model.

According to an embodiment, the electronic apparatus 1000 may convert the received data about the plurality of materials and the result of predicting the electronic structure of the plurality of materials into recognition data to be applied to the trained model. For example, a plurality of energy level-by-level state density graphs of the plurality of materials may be converted respectively into a plurality of lattice images. However, the inventive concept is not limited thereto.

In operation 330, the electronic apparatus 1000 may determine a standard for predicting an electronic structure of the material by using the recognition data applied to the trained model.

According to an embodiment, the electronic apparatus 1000 may determine a standard for predicting an electronic structure of the material by using the plurality of lattice images. The standard for predicting the electronic structure of the material may be a principal component for generating an energy level-by-level state density graph of the material. For example, the electronic apparatus 1000 may determine a coefficient of the principal component as a standard for predicting an electronic structure of the material. Also, the electronic apparatus 1000 may determine a relationship between the coefficient of the principal component and the d-orbital electron number occupation rate of each of a plurality of elements constituting the material as the standard for predicting the electronic structure of the material.

According to an embodiment, the electronic apparatus 1000 may predict the electronic structure of the material by using the determined standard. The electronic apparatus 1000 may output the result of predicting the electronic structure of the material.

According to an embodiment, the electronic apparatus 1000 may apply the electronic structure of the material predicted by the electronic apparatus 1000 as the training data to the trained model.

Figure 4:
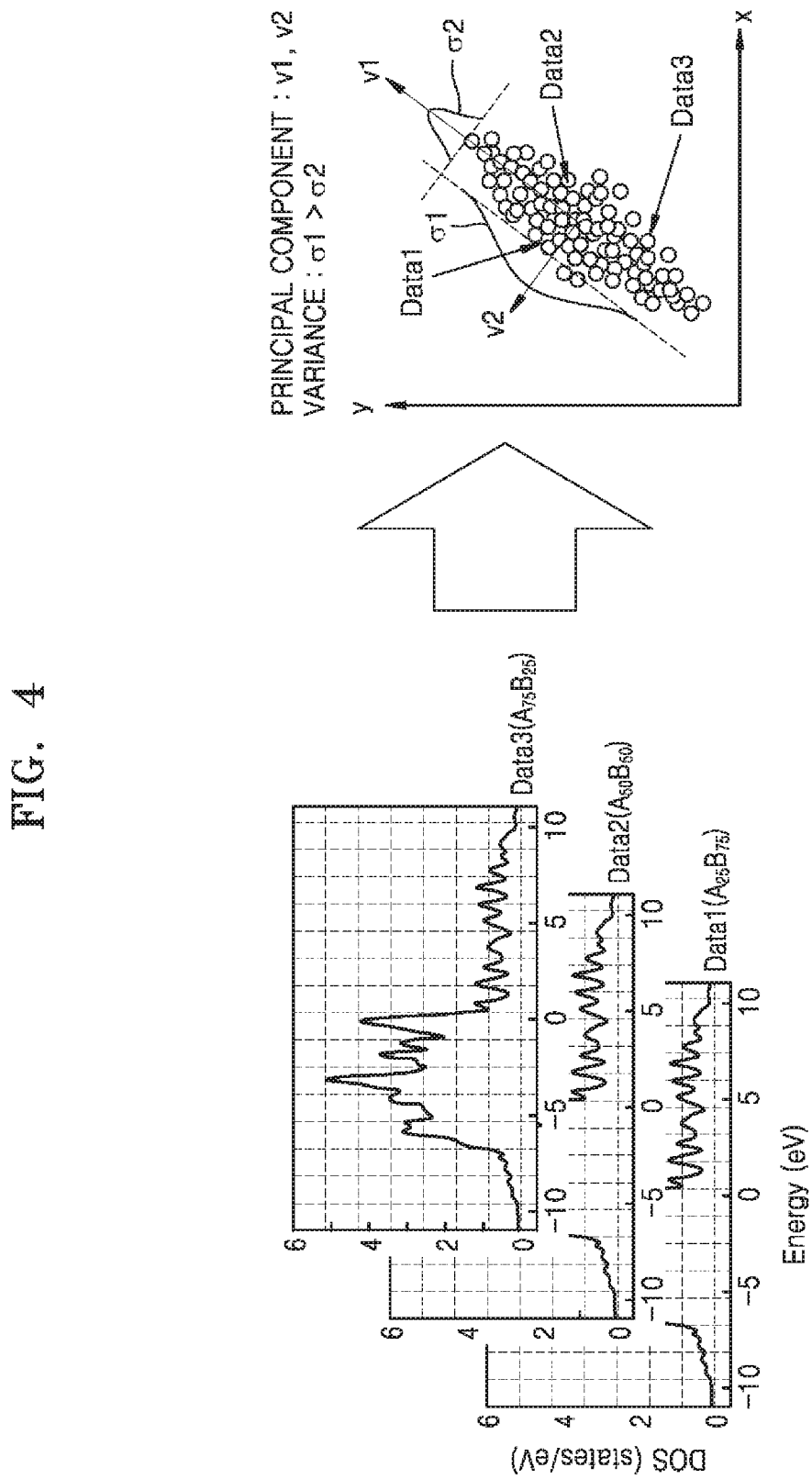
FIG. 4 is a diagram illustrating determining principal components of a plurality of energy level-by-level state density graphs of a material input, according to an embodiment.

FIG. 4 is a diagram illustrating determining principal components of a plurality of energy level-by-level state density graphs of a material input, according to an embodiment.

According to an embodiment, the electronic apparatus 1000 may determine principal components v1 and v2 for generating an energy level-by-level state density graph of a material by using a plurality of received data about elements of various materials and state density data of the material corresponding to each of the plurality of data. The state density data of the material may include, but is not limited to, an energy level-by-level state density graph.

For example, the electronic apparatus 1000 may receive data about elements included in Data1, data about elements included in Data2, and data about elements included in Data3, as input data from the user. Also, the electronic apparatus 1000 may receive an energy level-by-level state density graph included in Data1, an energy level-by-level state density graph included in Data2, and an energy level-by-level state density graph included in Data3 as input data from the user. The electronic apparatus 1000 may receive a plurality of input data including Data1, Data2, and Data3 from the user.

According to an embodiment, the electronic apparatus 1000 may convert each of the plurality of input data including Data1, Data2, and Data3 into recognition data to be applied to a trained model. For example, the electronic apparatus 1000 may convert a plurality of energy level-by-level state density graphs included in the plurality of input data including Data1, Data2, and Data3 into a plurality of lattice images. The electronic apparatus 1000 may convert the plurality of lattice images into a plurality of matrixes.

According to an embodiment, the electronic apparatus 1000 may determine principal components of the plurality of matrixes based on the plurality of matrixes. For example, the electronic apparatus 1000 may determine the principal components of the plurality of matrixes through a principal component analysis (PCA) of the plurality of matrixes. As a particular example, the electronic apparatus 1000 may calculate a covariance of the plurality of matrixes. The electronic apparatus 1000 may calculate at least one eigenvector and at least one eigenvalue based on the calculated covariance. The electronic apparatus 1000 may determine the principal components of the plurality of matrixes by using the at least one eigenvector and the at least one eigenvalue.

Referring to the right graph of FIG. 4, the electronic apparatus 1000 may represent each of a plurality of input data as a graph. A plurality of circles represented in the graph may correspond respectively to the plurality of input data Data1, Data2, and Data3 input from the user. The electronic apparatus 1000 may determine variance values σ1 and σ2 of a plurality of energy level-by-level state density graphs from the graph. The electronic apparatus 1000 may determine principal components v1 and v2 of the plurality of energy level-by-level state density graphs based on the determined variance values σ1 and σ2. For example, the variance value σ2 in the right upward direction of the graph is smaller than the variance value σ1 in the left upward direction of the graph. Thus, the electronic apparatus 1000 may determine the first principal component v1 in the upward direction and the second principal component v2 in the left upward direction. Although FIG. 4 illustrates the determination of two principal components, this is only for describing the determination of principal components and the inventive concept is not limited thereto.

Figure 5:
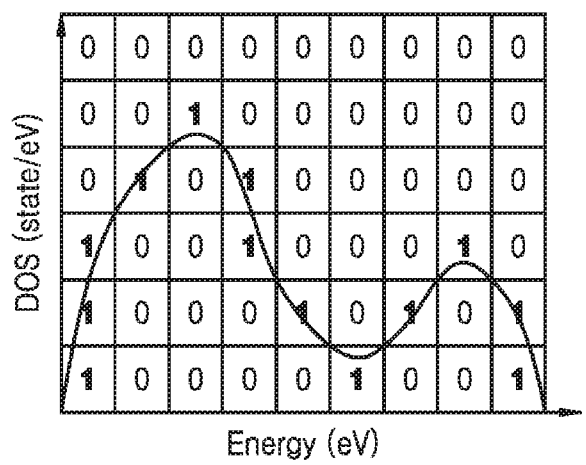
FIG. 5 is a diagram illustrating converting an energy level-by-level state density graph of a material converted into a lattice image into recognition data to be applied to a trained model, according to an embodiment.

FIG. 5 is a diagram illustrating converting an energy level-by-level state density graph of a material converted into a lattice image into recognition data for application to a trained model, according to an embodiment.

According to an embodiment, the electronic apparatus 1000 may convert each of a plurality of energy level-by-level state density graphs of a plurality of materials into a lattice image including a predetermined number of lattices. The electronic apparatus 1000 may convert each of a plurality of energy level-by-level state density graphs of a plurality of materials into a lattice image including N×M lattices (N is a natural number and M is a natural number).

According to an embodiment, the electronic apparatus 1000 may input a value of 1 to the grids corresponding to an energy level-by-level state density function curve constituting an energy level-by-level state density graph of a material among the grids constituting a lattice image, and input a value of 0 to the other lattices.

According to an embodiment, the electronic apparatus 1000 may convert a lattice image in which a data value is input to each of a plurality of lattices into a matrix. For example, the electronic apparatus 1000 may convert a lattice image in which a data value is input to each of a plurality of lattices into an N×M matrix.

According to an embodiment, the electronic apparatus 1000 may calculate a covariance of a plurality of matrixes converted therefrom. The electronic apparatus 1000 may calculate at least one eigenvector and at least one eigenvalue based on the calculated covariance.

According to an embodiment, the electronic apparatus 1000 may determine a principal component for generating an energy level-by-level state density graph of a material by using the calculated at least one eigenvector and at least one eigenvalue. For example, the electronic apparatus 1000 may determine the principal component having a higher priority in descending order of eigenvalues among a plurality of calculated eigenvectors.

According to an embodiment, the electronic apparatus 1000 may determine the number of principal components for generating an energy level-by-level state density graph of a material. The number of principal components may be determined based on a plurality of data about the elements constituting the material, but is not limited thereto. For example, the number of principal components may be determined based on the number of elements constituting the material, the type of the element, the number of atoms thereof, the number of electrons thereof, the chemical formula thereof, and the empirical formula thereof, but is not limited thereto. The number of principal components may be determined based on user's input data about the elements constituting the material, but is not limited thereto.

According to an embodiment, the principal component determined in the trained model used in the energy level-by-level state density graph of the material output from the trained model may be determined based on user's input data about the elements constituting the material, but is not limited thereto. For example, when two elements constitute a material, the electronic apparatus 1000 may determine the number of principal components for generating an energy level-by-level state density graph to be 2 to 4 based on the number of elements, the type of the elements, the number of atoms thereof, the number of electrons thereof, the chemical formula thereof, and the empirical formula thereof. The electronic apparatus 1000 may determine a principal component corresponding to a dimension having a small variance value as a principal component for generating an energy level-by-level state density graph based on the determined number of principal components.

According to an embodiment, the electronic apparatus 1000 may determine a coefficient of the principal component. The electronic apparatus 1000 may generate an energy level-by-level state density graph by using the determined principal component and the determined number of principal components. The electronic apparatus 1000 may determine a coefficient of the principal component by comparing the generated energy level-by-level state density graph and the energy level-by-level state density graph included in the training data.

Figure 6:
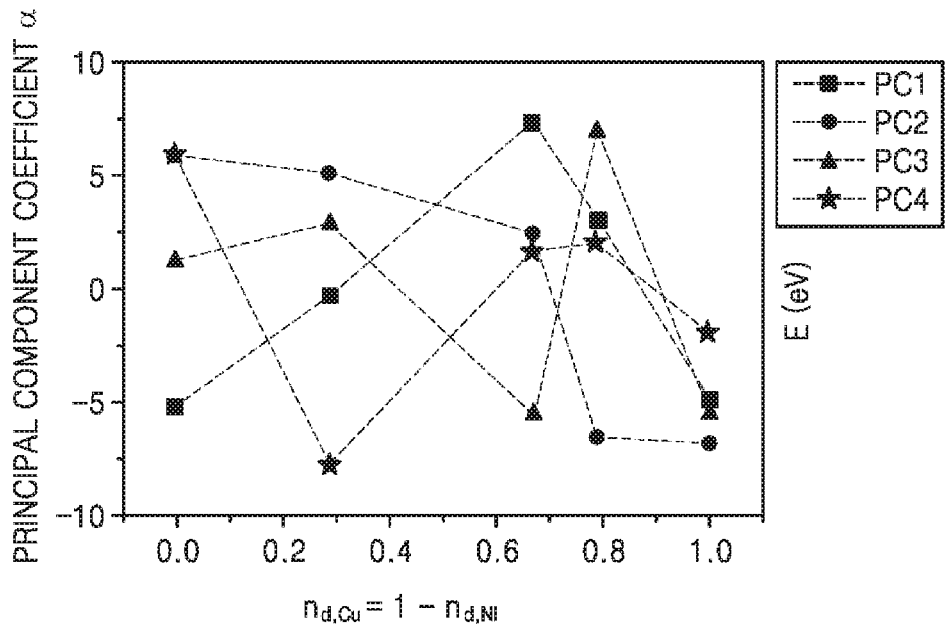
FIGS. 6 and 7 are graphs illustrating a relationship between an extracted principal component coefficient and a d-orbital electron number, according to an embodiment.
Figure 7:
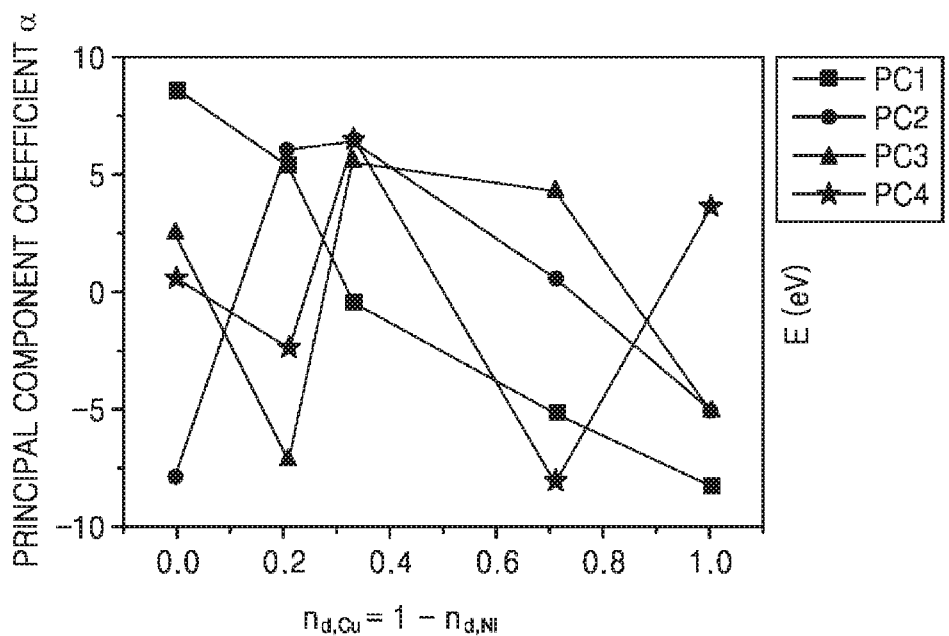

FIGS. 6 and 7 are graphs illustrating the relationship between an extracted principal component coefficient and a d-orbital electron number, according to an embodiment. In detail, FIG. 6 is a graph illustrating the relationship between the d-orbital electron number occupation rate of Cu and the coefficient of four principal components, and FIG. 7 is a graph illustrating the relationship between the d-orbital electron number occupation rate of Ni and the coefficient of four principal components.

According to an embodiment, the electronic apparatus 1000 may acquire a d-orbital electron number occupation rate of each of a plurality of elements based on user's input data about a plurality of elements constituting a material. The d-orbital electron number occupation rate of an element may mean the occupation rate of the number of d-orbital electrons included in at least one element constituting the material among the number of d-orbital electrons included in the material. For example, when elements constituting a material are A and B, the number of d-orbital electrons of A is a, the number of d-orbital electrons of B is b, the number of atoms of A is x, and the number of atoms of B is y, a d-orbital electron number occupation rate $n_{d,A}[A_xB_y]$ of A in a material $[A_xB_y]$ may be calculated by Equation 2. Also, a d-orbital electron number occupation rate $n_{d,B}[A_xB_y]$ of B in a material $[A_xB_y]$ may be calculated by Equation 3.

$$n_{d,A}[A_xB_y]: \frac{a \cdot x/(x+y)}{a \cdot x/(x+y) + b \cdot y/(x+y)} \quad \text{Equation 2}$$

$$n_{d,B} = 1 - n_{d,A} \quad \text{Equation 3}$$

As a particular example, when the element A is Cu and the element B is Ni, since the electron arrangement of Cu is $[Ar]3d^{10}4s^1$ and the electronic arrangement of Ni is $[Ar]3d^84s^2$, the number of d-orbital electrons of Cu is 10 and the number of d-orbital electrons of Ni is 8. A d-orbital electron number occupation rate $n_{d,Cu}[Cu_{50}Ni_{50}]$ of Cu in a material $[Cu_{50}Ni_{50}]$ having a Cu atom number of 50 and an Ni atom number of 50 is 0.67, and a d-orbital electron number occupation rate $n_{d,Ni}[Cu_{50}Ni_{50}]$ of Ni is 0.33.

According to an embodiment, the electronic apparatus 1000 may determine the relationship between a d-orbital electron number occupation rate of each of a plurality of elements constituting the material and a coefficient of a principal component for generating an energy level-by-level state density graph of the material. For example, the electronic apparatus 1000 may determine the coefficient of the principal component based on a graph about the principal component coefficient and the d-orbital electron number occupation rate of the elements constituting the material.

According to an embodiment, the electronic apparatus 1000 may generate a graph about the principal component coefficient and the d-orbital electron number occupation rate of each of a plurality of elements constituting a material, based on a plurality of data about a plurality of elements constituting elements included in the training data and an energy level-by-level state density graph included in the training data. For example, in the case of a material including Cu and Ni, the electronic apparatus 1000 may generate a graph about a d-orbital electron number occupation rate ($n_{d,Cu}$, $n_{d,Ni}$) of each of Cu and Ni constituting the material and coefficients (α1, α2, α3, α4) of principal components (PC1, PC1, PC2, PC3, PC4).

Referring to FIG. 6, the electronic apparatus 1000 may determine the principal components PC1, PC2, PC3, and PC4 based on the energy level-by-level state density graph of the material including Cu and Ni. The electronic apparatus 1000 may generate a graph about the coefficients α1, α2, α3, and α4 of the principal components PC1, PC2, PC3, and PC4 and the d-orbital electron number occupation rate $n_{d,Cu}$ of Cu. For example, when the d-orbital electron number occupation rate of Cu is 1, when the d-orbital electron number occupation rate of Cu is 0.8, when the d-orbital electron number occupation rate of Cu is 0.6, when the d-orbital electron number occupation rate of Cu is 0.3, or when the d-orbital electron number occupation rate of Cu is 0, the electronic apparatus 1000 may determine the respective coefficients of the corresponding principal components PC1, PC2, PC3, and PC4 in each case. The electronic apparatus 1000 may generate a graph about the determined coefficients α1, α2, α3, and α4 of the principal components PC1, PC2, PC3, and PC4 and the d-orbital electron number occupation rate $n_{d,Cu}$ of Cu.

Referring to FIG. 7, the electronic apparatus 1000 may determine the principal components PC1, PC2, PC3, and PC4 based on the energy level-by-level state density graph of the material including Cu and Ni. The electronic apparatus 1000 may generate a graph about the coefficients α1, α2, α3, and α4 of the principal components PC1, PC2, PC3, and PC4 and the d-orbital electron number occupation rate $n_{d,Ni}$ of Ni. For example, when the d-orbital electron number occupation rate of Ni is 1, when the d-orbital electron number occupation rate of Ni is 0.7, when the d-orbital electron number occupation rate of Ni is 0.4, when the d-orbital electron number occupation rate of Ni is 0.2, or when the d-orbital electron number occupation rate of Ni is 0, the electronic apparatus 1000 may determine the respective coefficients of the corresponding principal components PC1, PC2, PC3, and PC4 in each case. The electronic apparatus 1000 may generate a graph about the determined coefficients α1, α2, α3, and α4 of the principal components PC1, PC2, PC3, and PC4 and the d-orbital electron number occupation rate $n_{d,Ni}$ of Ni.

According to an embodiment, the electronic apparatus 1000 may determine a principal component coefficient of the material whose electronic structure is to be predicted, based on a graph about the principal component coefficient and the d-orbital electron number occupation rate of the elements constituting the material. For example, from the graph of FIG. 6, the electronic apparatus 1000 may determine the coefficients α1, α2, α3, and α4 of the principal components PC1, PC2, PC3 of the material whose electronic structure is to be predicted, among the materials including Cu and Ni. Also, from the graph of FIG. 7, the electronic apparatus 1000 may determine the coefficients α1, α2, α3, and α4 of the principal components PC1, PC2, PC3, and PC4 of the material whose electronic structure is to be predicted from among the materials including Cu and Ni.

Figure 8:
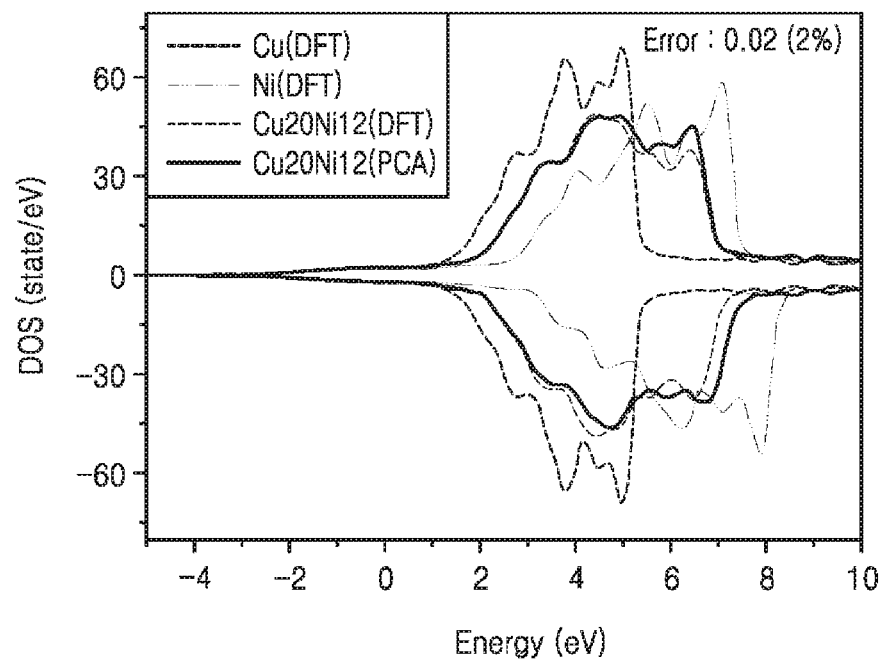
FIG. 8 illustrates a comparison between an estimated energy level-by-level state density graph and a DFT-based estimated energy level-by-level state density graph, according to an embodiment.
Figure 9:
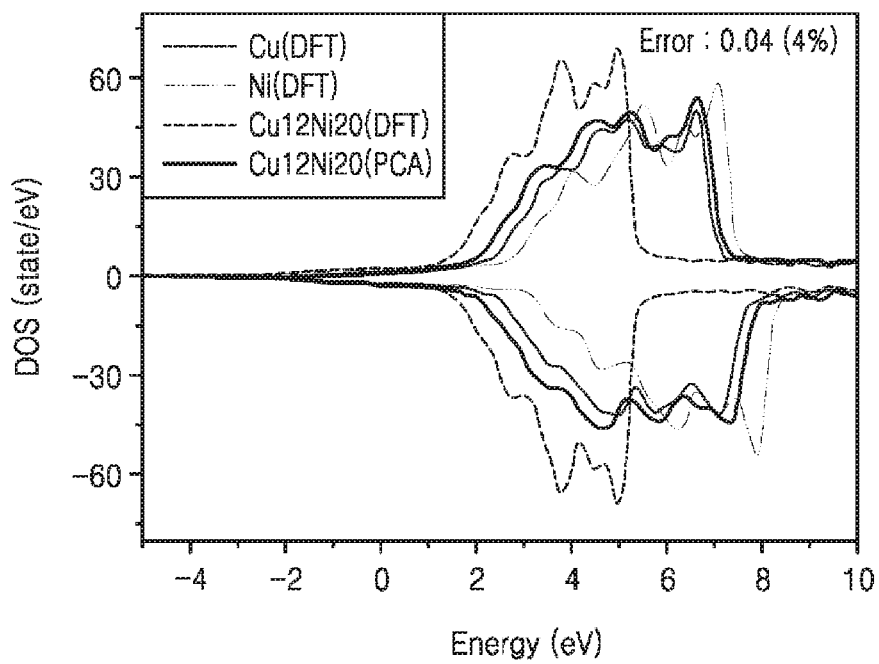
FIG. 9 illustrates a comparison between an estimated energy level-by-level state density graph and a DFT-based estimated energy-state density graph, according to an embodiment.

FIGS. 8 and 9 illustrate a comparison between an estimated energy level-by-level state density graph and a DFT-based estimated energy level-by-level state density graph, according to an embodiment.

Referring to FIG. 8, in the case of a material including Cu and Ni having a face-centered cubic (FCC), when the percentage of Cu is 100%, when the percentage of Cu is 75% and the percentage of Ni is 25%, when the percentage of Cu is 50% and the percentage of Ni is 50%, when the percentage of Cu is 25% and the percentage of Ni is 75%, or when the percentage of Ni is 100%, the electronic apparatus 1000 may receive data about elements constituting the material and an energy level-by-level state density graph of the material as training data in each case. The electronic apparatus 1000 may convert the received training data into recognition data. Since the recognition data has been described above, redundant descriptions thereof will omitted for conciseness.

The electronic apparatus 1000 may apply the recognition data to the trained model to determine the principal component of the material including Cu and Ni. The electronic apparatus 1000 may determine the coefficient of each of the principal components of the material whose electronic structure is to be predicted, among the materials including Cu and Ni. The electronic apparatus 1000 may generate an energy level-by-level state density graph of the material whose electronic structure is to be predicted, by using the determined principal component and the determined principal component coefficient.

The electronic apparatus 1000 may output the generated energy level-by-level state density graph. For example, when applying data about elements constituting a material [$Cu_{20}Ni_{12}$] whose electronic structure is to be predicted to the trained model, the electronic apparatus 1000 may output an energy level-by-level state density graph of the material [$Cu_{20}Ni_{12}$] output from the trained model. Also, when applying data about elements constituting a material [$Cu_{12}Ni_{20}$] whose electronic structure is to be predicted to the trained model, the electronic apparatus 1000 may output an energy level-by-level state density graph of the material [$Cu_{12}Ni_{20}$] output from the trained model.

Referring to FIG. 8, the energy level-by-level state density graph of the material [$Cu_{20}Ni_{12}$] output when the data about the elements constituting the material [$Cu_{20}Ni_{12}$] was applied to the trained model and the energy level-by-level state density graph of the material [$Cu_{20}Ni_{12}$] estimated by using the DFT showed only a difference (error) of 2%. However, the energy level-by-level state density graph of the material [$Cu_{20}Ni_{12}$] output when the data about the elements constituting the material [$Cu_{20}Ni_{12}$] was applied to the trained model was output in 3 minutes, and the energy level-by-level state density graph of the material [$Cu_{20}Ni_{12}$] estimated by using the DFT was output in 49 hours.

Referring to FIG. 9, the energy level-by-level state density graph of the material [$Cu_{12}Ni_{20}$] output when the data about the elements constituting the material [$Cu_{12}Ni_{20}$] was applied to the trained model and the energy level-by-level state density graph of the material [$Cu_{12}Ni_{20}$] estimated by using the DFT showed only a difference (error) of 4%. However, the energy level-by-level state density graph of the material [$Cu_{12}Ni_{20}$] output when the data about the elements constituting the material [$Cu_{12}Ni_{20}$] was applied to the trained model was output in 3 minutes, and the energy level-by-level state density graph of the material [$Cu_{12}Ni_{20}$] estimated by using the DFT was output in 49 hours.

That is, referring to FIGS. 8 and 9, it may be seen that the case of estimating the energy level-by-level state density graph of the material by using the trained model of the described embodiment may save more time than the case of estimating the energy level-by-level state density graph of the material by using the conventional DFT and there may be no difference in accuracy.

Also, the trained model of the described embodiment may increase the accuracy as the data about the elements of the material and the data about the electronic structure of the material are increased.

FIGS. 8 and 9 illustrate the case where two elements constitute a material, and show the comparison between the case of estimating the energy level-by-level state density graph of the material by using the trained model of the described embodiment and the case of estimating the energy level-by-level state density graph of the material by using the conventional DFT. As the elements constituting the material are increased, the case of estimating the energy level-by-level state density graph of the material by using the trained model of the described embodiment may save more time than the case of estimating the energy level-by-level state density graph of the material by using the conventional DFT.

Figure 10:
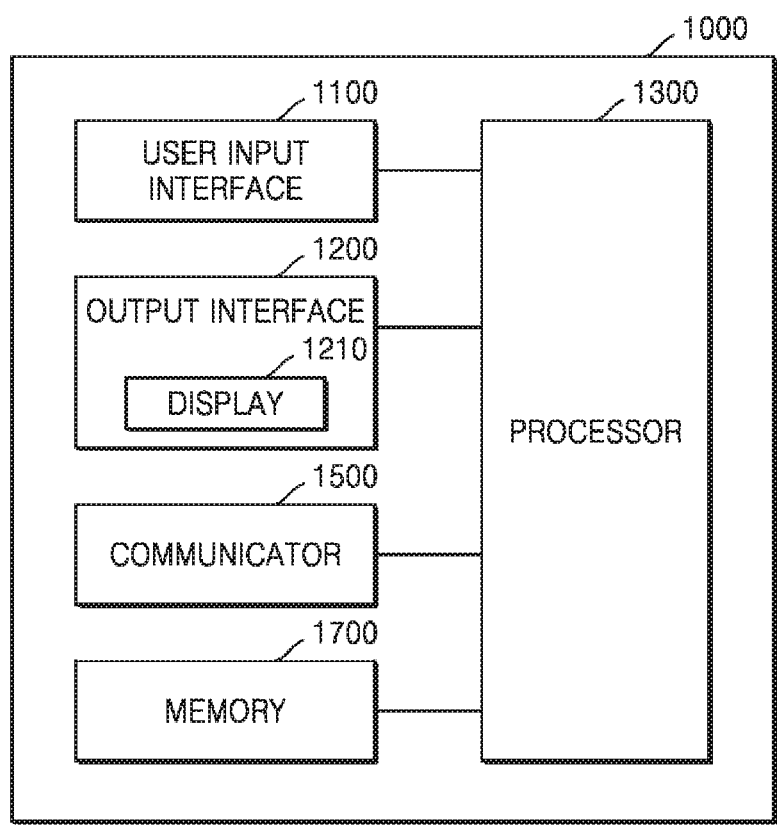
FIG. 10 is a block diagram of an electronic apparatus according to an embodiment.

FIG. 10 is a block diagram of an electronic apparatus according to an embodiment.

Referring to FIG. 10, an electronic apparatus 1000 according to some embodiments may include a user input interface 1100, an output interface 1200, a processor 1300, a communicator 1500, and a memory 1700. However, not all of the components illustrated in FIG. 10 are necessary components of the electronic apparatus 1000. The electronic apparatus 1000 may be implemented by more components than the components illustrated in FIG. 10, or may be implemented by less components than the components illustrated in FIG. 10.

The user input interface 1100 may refer to a unit through which the user inputs data for controlling the electronic device 1000. For example, the user input interface 1100 may include, but is not limited to, a keypad, a dome switch, a touch pad (e.g., a capacitive overlay type, a resistive overlay type, an infrared beam type, a surface acoustic wave type, an integral strain gauge type, or a piezoelectric type), a jog wheel, and a jog switch.

The output interface 1200 may display and output information processed by the electronic apparatus 1000. The output interface 1200 may include a display 1210 for outputting the prediction result of an electronic structure of a material. For example, the display 1210 may display an energy level-by-level state density graph of the material corresponding to user's input data about elements constituting the material. The display 1210 may display a user interface for receiving an input of data about the elements constituting the material.

In general, the processor 1300 may control an overall operation of the electronic apparatus 1000. For example, the processor 1300 may control overall operations of the user input interface 1100, the output interface 1200, and the communicator 1500 by executing programs stored in the memory 1700. Also, by executing the programs stored in the memory 1700, the processor 1300 may perform the functions of the electronic apparatus 1000 illustrated in FIGS. 1 to 7.

The processor 1300 may control the user input interface 1100 to receive an input of the data about the elements constituting the material. The processor 1300 may predict an electronic structure of the material based on the data input from the user. The processor 1300 may output a prediction result of the electronic structure of the material.

According to an embodiment, the processor 1300 may predict the electronic structure of the material by applying the data about the number of elements constituting the material, the type of the elements, the number of atoms thereof, the number of electrons thereof, the chemical formula thereof, and the empirical formula thereof, which is input from the user, to a trained model for estimating a state density of the material.

According to an embodiment, in order to predict the electronic structure of the material, the processor 1300 may generate an energy level-by-level state density graph of the material and output the generated energy level-by-level state density graph.

According to an embodiment, the processor 1300 may receive data about a plurality of materials and the result of predicting an electronic structure of the plurality of materials as the training data from the user.

According to an embodiment, the processor 1300 may convert the training data received from the user into recognition data for application to the trained model. The processor 1300 may apply the recognition data to the trained model. For example, the processor 1300 may convert energy level-by-level state density graphs of the plurality of materials respectively into lattice images. The processor 1300 may convert the lattice images into matrixes.

According to an embodiment, the processor 1300 may determine a standard for predicting an electronic structure of the material by using the recognition data applied to the trained model. For example, the processor 1300 may determine a standard for predicting an electronic structure of the material by using the lattice images. The processor 1300 may determine a principal component for generating an energy level-by-level state density graph of the material as a standard for predicting an electronic structure of the material. The processor 1300 may determine the number of principal components as a standard for predicting an electronic structure of the material. The processor 1300 may determine a coefficient of the principal component as a standard for predicting an electronic structure of the material. The processor 1300 may determine the relationship between the coefficient of the principal component and the d-orbital electron number occupation rate of each of a plurality of elements constituting the material as the standard for predicting the electronic structure of the material.

For example, the processor 1300 may convert a plurality of energy level-by-level state density graphs included in a plurality of input data into a plurality of lattice images. The processor 1300 may convert the plurality of lattice images into a plurality of matrixes. The processor 1300 may determine principal components of the plurality of matrixes based on the plurality of matrixes. The processor 1300 may determine the principal components of the plurality of matrixes through a principal component analysis (PCA) on the plurality of matrixes. The processor 1300 may calculate a covariance of the plurality of matrixes. The processor 1300 may calculate at least one eigenvector and at least one eigenvalue based on the calculated covariance. The processor 1300 may determine the principal components of the plurality of matrixes by using the at least one eigenvector and the at least one eigenvalue.

According to an embodiment, the processor 1300 may determine a coefficient of the principal component by comparing the generated energy level-by-level state density graph and the energy level-by-level state density graph included in the training data.

According to an embodiment, the processor 1300 may acquire a d-orbital electron number occupation rate of each of a plurality of elements based on user's input data about a plurality of elements constituting a material. The processor 1300 may determine the relationship between a d-orbital electron number occupation rate of each of a plurality of elements constituting the material and a coefficient of a principal component for generating an energy level-by-level state density graph of the material. The processor 1300 may generate a graph about the principal component coefficient and the d-orbital electron number occupation rate of each of a plurality of elements constituting a material, based on a plurality of data about a plurality of elements constituting elements included in the training data and an energy level-by-level state density graph included in the training data. The processor 1300 may determine a principal component coefficient of the material whose electronic structure is to be predicted, based on a graph about the principal component coefficient and the d-orbital electron number occupation rate of the elements constituting the material.

According to an embodiment, the processor 1300 may predict the electronic structure of the material by using the determined standard. The processor 1300 may output a prediction result of the electronic structure of the material. For example, the processor 1300 may generate an energy level-by-level state density graph by using the determined principal component, the determined number of principal components, and the determined principal component coefficient.

According to an embodiment, the processor 1300 may apply the electronic structure of the material predicted by the processor 1300 as the training data to the trained model.

Also, by using a data recognition model stored in the memory 1700 or a server 2000, the processor 1300 may predict an electronic structure of the material corresponding to the user's input data about the elements constituting the material.

Also, by using a data recognition model stored in the memory 1700 or the server 2000, the processor 1300 may efficiently train a standard for predicting an electronic structure of the material corresponding to the user's input data about the elements constituting the material and may rapidly and accurately predict an electronic structure of the material according to the training result.

The communicator 1500 may include one or more components for allowing the electronic apparatus 1000 to communicate with another apparatus (not illustrated) and the server 2000. The other apparatus (not illustrated) may be, but is not limited to, a sensing apparatus or a computing apparatus such as the electronic apparatus 1000.

Also, the communicator 1500 may transmit/receive information necessary for executing an operation of predicting an electronic structure of the material corresponding to the user's input data about the elements constituting the material to/from another apparatus (not illustrated) and the server 2000.

The memory 1700 may store one or more programs for processing and controlling the operations of the processor 1300, and may store data that is input to the electronic apparatus 1000 or output from the electronic apparatus 1000.

The memory 1700 may include at least one type of storage medium from among flash memory type, hard disk type, multimedia card micro type, card type memory (e.g., SD or XD memory), random-access memory (RAM), static random-access memory (SRAM), read-only memory (ROM), electronically erasable programmable read-only memory (EEPROM), programmable read-only memory (PROM), magnetic memory, magnetic disk, and optical disk.

Figure 11:
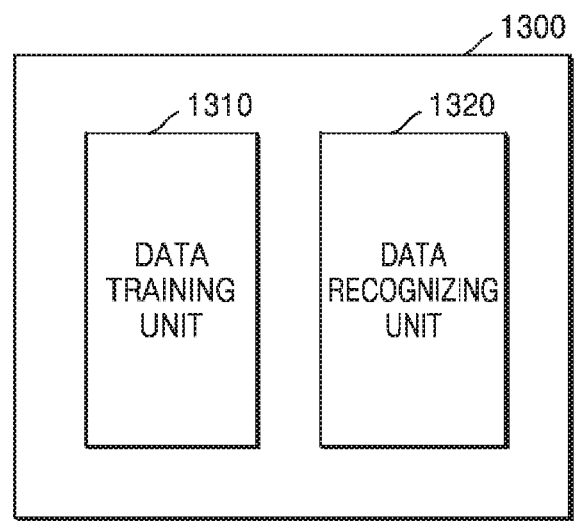
FIG. 11 is a block diagram of a processor of an electronic apparatus according to an embodiment.

FIG. 11 is a block diagram of a processor of an electronic apparatus according to an embodiment.

Referring to FIG. 11, a processor 1300 according to some embodiments may include a data training unit 1310 and a data recognizing unit 1320.

The data training unit 1310 may train a standard for predicting an electronic structure of a material corresponding to user's input data about elements constituting the material.

By using a trained data recognition model, the data recognizing unit 1320 may predict an electronic structure of the material corresponding to the user's input data about the elements constituting the material. The data recognizing unit 1320 may acquire predetermined data according to a predetermined standard obtained by training, and may use a data recognition model with the acquired data as an input value. Also, a result value output by the data recognition model with the acquired data as an input value may be used to refine the data recognition model.

At least one of the data training unit 1310 and the data recognizing unit 1320 may be manufactured in the form of at least one hardware chip and mounted on the electronic apparatus. For example, at least one of the data training unit 1310 and the data recognizing unit 1320 may be manufactured in the form of a dedicated hardware chip for artificial intelligence (AI) or may be manufactured as a portion of a general-purpose processor (e.g., a CPU or an application processor) or a graphic processor (e.g., a GPU) and mounted on various electronic apparatuses described above.

In this case, the data training unit 1310 and the data recognizing unit 1320 may be mounted on one electronic apparatus or on respective separate electronic apparatuses. For example, one of the data training unit 1310 and the data recognizing unit 1320 may be included in the electronic apparatus, and the other may be included in the server. Also, by wired or wireless communication, the data training unit 1310 and the data recognizing unit 1320 may provide the model information generated by the data training unit 1310 to the data recognizing unit 1320, and the data input to the data recognizing unit 1320 may be provided as additional training data to the data training unit 1310.

Meanwhile, at least one of the data training unit 1310 and the data recognizing unit 1320 may be implemented as a software module. When at least one of the data training unit 1310 and the data recognizing unit 1320 is implemented as a software module (or a program module including instructions), the software module may be stored in a non-transitory computer-readable recording medium. Also, in this case, at least one software module may be provided by an operating system (OS) or by a predetermined application. Alternatively, some of the at least one software module may be provided by an operating system (OS), and the others may be provided by a predetermined application.

Figure 12:
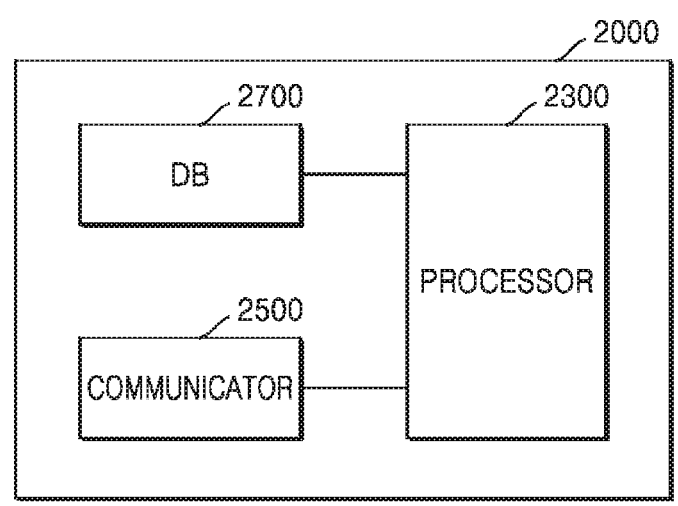
FIG. 12 is a block diagram of a server interacting with an electronic apparatus according to an embodiment.

FIG. 12 is a block diagram of a server interacting with an electronic apparatus according to an embodiment.

Referring to FIG. 12, a server 2000 according to some embodiments may include a communicator 2500, a database (DB) 2700, and a processor 2300.

The communicator 2500 may include one or more components for allowing communication with the electronic apparatus 1000.

The DB 2700 may store a program and data for predicting an electronic structure of a material corresponding to user's input data about elements constituting the material.

In general, the processor 2300 may control an overall operation of the server 2000. For example, the processor 2300 may control the overall operations of the DB 2700 and the communicator 2500 by executing the programs stored in the DB 2700 of the server 2000. By executing some of the programs stored in the DB 2700, the processor 2300 may perform some of the functions of the electronic apparatus 1000 illustrated in FIGS. 1 to 7.

Also, the processor 2300 may predict an electronic structure of the material corresponding to the user's input data about the elements constituting the material.

Also, by using a data recognition model stored in the DB 2700, the processor 2300 may efficiently train a standard for predicting an electronic structure of the material corresponding to the user's input data about the elements constituting the material and may accurately predict an electronic structure of the material according to the training result.

Meanwhile, the electronic apparatus 1000 and the server 2000 may effectively distribute and perform operations for data recognition and data recognition model training and thus may efficiently perform data processing to provide a service satisfying the user's intention and may effectively protect the user's privacy.

Some embodiments may also be implemented in the form of a computer-readable recording medium including instructions executable by a computer, such as program modules executed by a computer. The computer-readable recording medium may be any available medium accessible by a computer and may include all of volatile or non-volatile mediums and removable or non-removable mediums. Also, the computer-readable recording medium may include all of computer storage mediums and communication mediums.

The computer storage mediums may include all of volatile or non-volatile mediums and removable or non-removable mediums that are implemented by any method or technology to store information such as computer-readable instructions, data structures, program modules, or other data. The communication mediums may generally include computer-readable instructions, data structures, and program modules.

Also, herein, a "unit" may include a hardware component such as a processor or a circuit, and/or a software component executed by a hardware component such as a processor.

The foregoing is illustrative of embodiments of the inventive concept and is not to be construed as limiting thereof. Although the embodiments have been described above, those of ordinary skill in the art will readily understand that various modifications may be made therein without materially departing from the spirits or features of the inventive concept. Therefore, it is to be understood that the embodiments described above should be considered in a descriptive sense only and not for purposes of limitation. For example, elements described as being combined may also be implemented in a distributed manner, and elements described as being distributed may also be implemented in a combined manner.

Therefore, the scope of the inventive concept is defined not by the detailed description of the embodiments but by the appended claims, and all modifications or differences within the scope should be construed as being included in the inventive concept.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of predicting an electronic structure of a material by an electronic apparatus, the method comprising:
    receiving a user's input data about elements constituting the material;
    applying the received user's input data to a trained model for estimating a state density of the material; and
    outputting a first graph representing energy level-by-level state densities of the material output from the trained model,
    wherein the trained model is trained to generate the first graph based on a plurality of second graphs representing pre-calculated energy level-by-level state densities respectively corresponding to a plurality of pre-input data about elements of various materials and the plurality of pre-input data by converting the plurality of second graphs into recognition data,
    wherein the converting the plurality of second graphs comprises:
    converting the plurality of second graphs into a plurality of lattice images, respectively;
    converting the plurality of lattice images into a plurality of matrixes, respectively;
    calculating a covariance of the plurality of matrixes;
    calculating at least one eigenvector and at least one eigenvalue based on the calculated covariance; and
    determining at least one principal component representing a characteristic of the first graph based on the at least one eigenvector and the at least one eigenvalue; and
    wherein the trained model is trained to generate the first graph based on the at least one principal component.

2. The method of claim 1, wherein the trained model is used to determine a number of principal components used to generate the first graph based on the user's input data.

3. The method of claim 2, wherein the trained model is trained to determine the at least one principal component used to generate the first graph based on the determined number of principal components.

4. The method of claim 1, wherein the trained model is trained to acquire, from the received user's input data, a d-orbital electron number occupation rate of each of a plurality of elements constituting the material and determine a coefficient of the at least one principal component based on the acquired d-orbital electron number occupation rate.

5. The method of claim 4, wherein the d-orbital electron number occupation rate is determined based on a number of atoms and a d-orbital electron number of each of the elements constituting the material.

6. An electronic apparatus for predicting an electronic structure of a material, the electronic apparatus comprising:
    a user input interface configured to receive a user's input data about elements constituting the material;
    a processor configured to apply the received user's input data to a trained model for estimating a state density of the material; and
    an output interface configured to output a first graph representing energy level-by-level state densities of the material output from the trained model,
    wherein the trained model is trained to generate the first graph based on a plurality of second graphs representing pre-calculated energy level-by-level state densities respectively corresponding to a plurality of pre-input data about elements of various materials and the plurality of pre-input data by converting the plurality of second graphs into recognition data,
    wherein the trained model is trained to:
    convert the plurality of second graphs into a plurality of lattice images, respectively,
    convert the plurality of lattice images into a plurality of matrixes, respectively,
    calculate a covariance of the plurality of matrixes,
    calculate at least one eigenvector and at least one eigenvalue based on the calculated covariance,
    determine at least one principal component representing a characteristic of the first graph based on the at least one eigenvector and the at least one eigenvalue and
    generate the first graph based on the at least one principal component.

7. The electronic apparatus of claim 6, wherein the trained model is trained to determine a number of principal components used to generate the first graph based on the user's input data.

8. The electronic apparatus of claim 7, wherein the trained model is trained to determine the at least one principal component used to generate the first graph based on the determined number of principal components.

9. The electronic apparatus of claim 6, wherein the trained model is trained to acquire, from the received user's input data, a d-orbital electron number occupation rate of each of a plurality of elements constituting the material and determine a coefficient of the at least one principal component based on the acquired d-orbital electron number occupation rate.

10. The electronic apparatus of claim 9, wherein the d-orbital electron number occupation rate is determined based on a number of atoms and a d-orbital electron number of each of constituent elements of the material.

11. A non-transitory computer-readable recording medium that stores a program that, when executed by a computer, performs the method of claim 1.

* * * * *